US011247899B2

(12) United States Patent
Lynn

(10) Patent No.: US 11,247,899 B2
(45) Date of Patent: *Feb. 15, 2022

(54) TRANSPORTABLE SYSTEM FOR CREATING AN OXIDATION REDUCTION POTENTIAL (ORP) IN WATER WITH PIPE ASSEMBLY FOR IN-LINE MIXING

(71) Applicant: Daniel W. Lynn, Omaha, NE (US)

(72) Inventor: Daniel W. Lynn, Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/408,742

(22) Filed: Aug. 23, 2021

(65) Prior Publication Data
US 2021/0380410 A1    Dec. 9, 2021

Related U.S. Application Data

(63) Continuation-in-part of application No. 17/391,152, filed on Aug. 2, 2021, and a continuation-in-part of
(Continued)

(51) Int. Cl.
  *C02F 1/78* (2006.01)
  *C11D 7/04* (2006.01)
  (Continued)

(52) U.S. Cl.
  CPC .............. *C01B 13/11* (2013.01); *A61L 2/183* (2013.01); *B01F 3/04503* (2013.01); *B01F 5/0428* (2013.01); *C02F 1/78* (2013.01); *C11D 3/48* (2013.01); *C11D 7/04* (2013.01); *C11D 11/0023* (2013.01); *C11D 11/0064* (2013.01);
  (Continued)

(58) Field of Classification Search
  USPC .... 204/157.5; 210/85, 87, 90, 96.1, 97, 136, 210/137, 150, 151, 192, 202, 259, 607, 210/614, 631, 724, 739, 741, 743, 746, 210/750, 760, 769; 261/76
  See application file for complete search history.

(56) References Cited

U.S. PATENT DOCUMENTS 6,153,105 A    11/2000  Tadlock et al.
6,334,328 B1    1/2002  Brill
(Continued)

OTHER PUBLICATIONS

International Search Report and Written Opinion for PCT/US2021/047089 dated Nov. 12, 2021.

*Primary Examiner* — Hayden Brewster
(74) *Attorney, Agent, or Firm* — Nasr Patent Law LLC; Faisal K. Abou-Nasr

(57) ABSTRACT

A transportable system for creating an oxidation reduction potential (ORP) in water employs a pipe assembly for in-line mixing. The pipe assembly includes a first flow path for water to flow through. The first flow path includes one or more ozone intake ports that are fluidically coupled to one or more ozone output ports of an ozone supply unit. The pipe assembly further includes a second flow path fluidically coupled in parallel with the first flow path. The second flow path includes a control valve that selectively permits a portion of the water to flow through the second flow path to produce a negative pressure in the first flow path so that ozone is drawn into the first flow path through the one or more ozone intake ports and mixed into the water flowing through the first flow path.

20 Claims, 9 Drawing Sheets

Related U.S. Application Data application No. 17/168,911, filed on Feb. 5, 2021, now Pat. No. 11,097,946, which is a continuation-in-part of application No. 17/150,499, filed on Jan. 15, 2021, now Pat. No. 11,078,079, said application No. 17/391,152 is a continuation-in-part of application No. 17/150,424, filed on Jan. 15, 2021, now Pat. No. 11,078,078, said application No. 17/150,449 is a continuation-in-part of application No. 17/078,799, filed on Oct. 23, 2020, which is a continuation of application No. 15/476,326, filed on Mar. 31, 2017, which is a continuation-in-part of application No. 15/446,331, filed on Mar. 1, 2017, now Pat. No. 10,232,070, which is a continuation-in-part of application No. 15/355,884, filed on Nov. 18, 2016, now abandoned, which is a continuation-in-part of application No. 15/050,777, filed on Feb. 23, 2016, now abandoned.

(60) Provisional application No. 62/121,770, filed on Feb. 27, 2015.

(51) Int. Cl.
    *C11D 3/48*          (2006.01)
    *C11D 11/00*         (2006.01)
    *C01B 13/11*         (2006.01)
    *B01F 3/04*          (2006.01)
    *A61L 2/18*          (2006.01)
    *B01F 5/04*          (2006.01)

(52) U.S. Cl.
    CPC .. *A61L 2202/11* (2013.01); *B01F 2003/04886* (2013.01); *C02F 2201/782* (2013.01); *C02F 2209/04* (2013.01); *C02F 2209/40* (2013.01); *C02F 2303/04* (2013.01)

(56) References Cited

U.S. PATENT DOCUMENTS

| | | | |
|---|---|---|---|
| 6,685,825 | B1 | 2/2004 | Chang |
| 8,071,526 | B2 | 12/2011 | Lynn |
| 8,075,705 | B2 | 12/2011 | Lynn |
| 9,068,149 | B2 | 6/2015 | Lynn |
| 9,151,528 | B2 | 10/2015 | Erbs et al. |
| 9,174,845 | B2 | 11/2015 | Lynn |
| 9,522,348 | B2 | 12/2016 | Lynn |
| 2002/0127158 | A1 | 9/2002 | Holsclaw et al. |
| 2004/0004042 | A1 | 1/2004 | Hadley et al. |
| 2004/0074252 | A1 | 4/2004 | Shelton |
| 2004/0168989 | A1 | 9/2004 | Tempest |
| 2009/0142225 | A1 | 6/2009 | Tornqvist |
| 2009/0185959 | A1 | 9/2009 | Weber et al. |
| 2009/0250407 | A1* | 10/2009 | Delano ............ C02F 9/00 210/748.12 |
| 2010/0219137 | A1 | 9/2010 | Lacasse |
| 2013/0193081 | A1 | 8/2013 | Vasiliu et al. |
| 2013/0341285 | A1 | 12/2013 | Marion |
| 2014/0027388 | A1 | 1/2014 | Constant |
| 2014/0263097 | A1 | 9/2014 | Lynn |
| 2016/0251243 | A1 | 9/2016 | Lynn |

\* cited by examiner

TRANSPORTABLE SYSTEM FOR CREATING AN OXIDATION REDUCTION POTENTIAL (ORP) IN WATER WITH PIPE ASSEMBLY FOR IN-LINE MIXING

CROSS-REFERENCE TO RELATED APPLICATIONS

The present application is a Continuation-in-Part of U.S. application Ser. No. 17/168,911 filed Feb. 5, 2021 entitled SYSTEM FOR CREATING AN OXIDATION REDUCTION POTENTIAL (ORP) IN WATER WITH PIPE ASSEMBLY FOR IN-LINE MIXING which is a Continuation-in-Part of U.S. application Ser. No. 17/150,449 filed Jan. 15, 2021 entitled SYSTEM FOR CREATING AN OXIDATION REDUCTION POTENTIAL (ORP) IN WATER WITH MULTI-PATH MANIFOLD FOR MIXING AND DISTRIBUTION which is a Continuation-in-Part of U.S. application Ser. No. 17/078,799 filed Oct. 23, 2020 entitled SYSTEMS AND METHODS FOR CREATING AN OXIDATION REDUCTION POTENTIAL (ORP) IN WATER FOR PATHOGENIC CLEANSING AND/OR DEGREASING OF HARD SURFACES AND EQUIPMENT which is a Continuation of U.S. application Ser. No. 15/476,326 filed Mar. 31, 2017 entitled SYSTEMS AND METHODS FOR CREATING AN OXIDATION REDUCTION POTENTIAL (ORP) IN WATER FOR PATHOGENIC CLEANSING AND/OR DEGREASING OF HARD SURFACES AND EQUIPMENT which is a Continuation-in-Part of U.S. application Ser. No. 15/446,331 filed Mar. 1, 2017 entitled SYSTEMS AND METHODS FOR CREATING AN OXIDATION REDUCTION POTENTIAL (ORP) IN WATER FOR PATHOGENIC CONTROL WITH THE WATER AND OZONE SOLUTIONS THEREOF BEING SUPPLIED TO ONE OR MORE WASH-DOWN STATIONS which is a Continuation-in-Part of U. S. application Ser. No. 15/355,884 filed Nov. 18, 2016 entitled SYSTEMS AND METHODS FOR CREATING AN OXIDATION REDUCTION POTENTIAL (ORP) IN WATER FOR PATHOGENIC CONTROL which is a Continuation-in-Part of U.S. application Ser. No. 15/050,777 filed Feb. 23, 2016 entitled SYSTEMS AND METHODS FOR CREATING AN OXIDATION REDUCTION POTENTIAL (ORP) IN WATER FOR PATHOGENIC CONTROL which claims the benefit of U.S. Provisional Application Ser. No. 62/121,770 filed Feb. 27, 2015 entitled SYSTEMS AND METHODS FOR CREATING AN OXIDATION REDUCTION POTENTIAL (ORP) IN WATER FOR PATHOGENIC CONTROL, all of which are incorporated by reference. The present application is also a Continuation-in-Part of U.S. application Ser. No. 17/391,152 filed Aug. 2, 2021 entitled MULTI-UNIT SYSTEM FOR CREATING AN OXIDATION REDUCTION POTENTIAL (ORP) IN WATER WITH MULTI-PATH MANIFOLD FOR MIXING AND DISTRIBUTION which is a Continuation-in-Part of U.S. application Ser. No. 17/150,424 filed Jan. 15, 2021 entitled MULTI-UNIT SYSTEM FOR CREATING AN OXIDATION REDUCTION POTENTIAL (ORP) IN WATER WITH MULTI-PATH MANIFOLD FOR MIXING AND DISTRIBUTION, all of which are incorporated by reference.

TECHNICAL FIELD

The present disclosure relates to systems for creating an oxidation reduction potential (ORP) in water for pathogenic control, and more particularly, to a system that employs a pipe assembly for in-line mixing of water and ozone solution.

BACKGROUND

Water intended for potable use (e.g., drinking water), may contain disease-causing organisms, or pathogens, which can originate from the source of the water, from resistance to water treatment techniques, from improper or ineffectual water treatment techniques, or so forth. Pathogens include various types of bacteria, viruses, protozoan parasites, and other organisms. To protect drinking water from disease-causing organisms, or pathogens, water suppliers often add a disinfectant, such as chlorine, to the water. However, disinfection practices can be ineffectual because certain microbial pathogens, such as *Cryptosporidium*, are highly resistant to traditional disinfection practices. Also, disinfectants themselves can react with naturally-occurring materials in the water to form byproducts, such as trihalomethanes and haloacetic acids, which may pose health risks.

A major challenge for water suppliers is how to control and limit the risks from pathogens and disinfection byproducts. It is important to provide protection from pathogens while simultaneously minimizing health risks to the population from disinfection byproducts. Oxidation reduction potential (ORP) can be used for water system monitoring to reflect the antimicrobial potential of the water, without regard to the water quality, with the benefit of a single-value measure of the disinfection potential, showing the activity of the disinfectant rather than the applied dose.

There are a number of systems that generate ORP in water by injecting ozone into the water to create an ozone and water solution. However, high pressure water applications present challenges, often requiring the use of an intermediate tank that must be filled prior to use (much like a water heater). To overcome such challenges, there is a need for improvements in the mixing and distribution of water and ozone solution.

SUMMARY

Aspects of this disclosure are directed to a transportable system for creating an oxidation reduction potential (ORP) in water using one or more pipe assemblies for in-line mixing of water and ozone solution. In embodiments, the system includes an ozone supply unit and a pipe assembly that are mounted to a transportable support frame (e.g., a wheeled support frame).

The ozone supply unit includes a supply unit enclosure having one or more air intake ports and one or more ozone output ports. A plurality of ozone generators are disposed within the supply unit enclosure. The plurality of ozone generators are fluidically coupled to the one or more air intake ports and the one or more ozone output ports of the supply unit enclosure. One or more controllers are also disposed within the supply unit enclosure. The one or more controllers are communicatively coupled to the plurality of ozone generators.

A flow switch may be included within and/or communicatively coupled to the ozone supply unit. The flow switch is configured to transmit one or more control signals to the one or more controllers in response to sensing a flow of water, where the one or more controllers are configured to cause the plurality of ozone generators to generate ozone in response to the one or more control signals. In some embodiments, the flow switch is coupled to or integrated within a flow path of the pipe assembly.

The pipe assembly includes a first flow path for water to flow through. The first flow path includes one or more ozone intake ports that are fluidically coupled to the one or more ozone output ports of the supply unit enclosure. The pipe assembly further includes a second flow path fluidically coupled in parallel with the first flow path. The second flow path includes a control valve that selectively permits a portion of the water to flow through the second flow path to produce a negative pressure in the first flow path so that ozone is drawn into the first flow path through the one or more ozone intake ports and mixed into the water flowing through the first flow path.

The supply unit enclosure and the pipe assembly may be fluidically coupled, e.g., by one or more tubes for transferring ozone from the supply unit enclosure to the pipe assembly. In embodiments, the supply unit enclosure and the pipe assembly are independently locatable, separate structures.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Figure 1A:
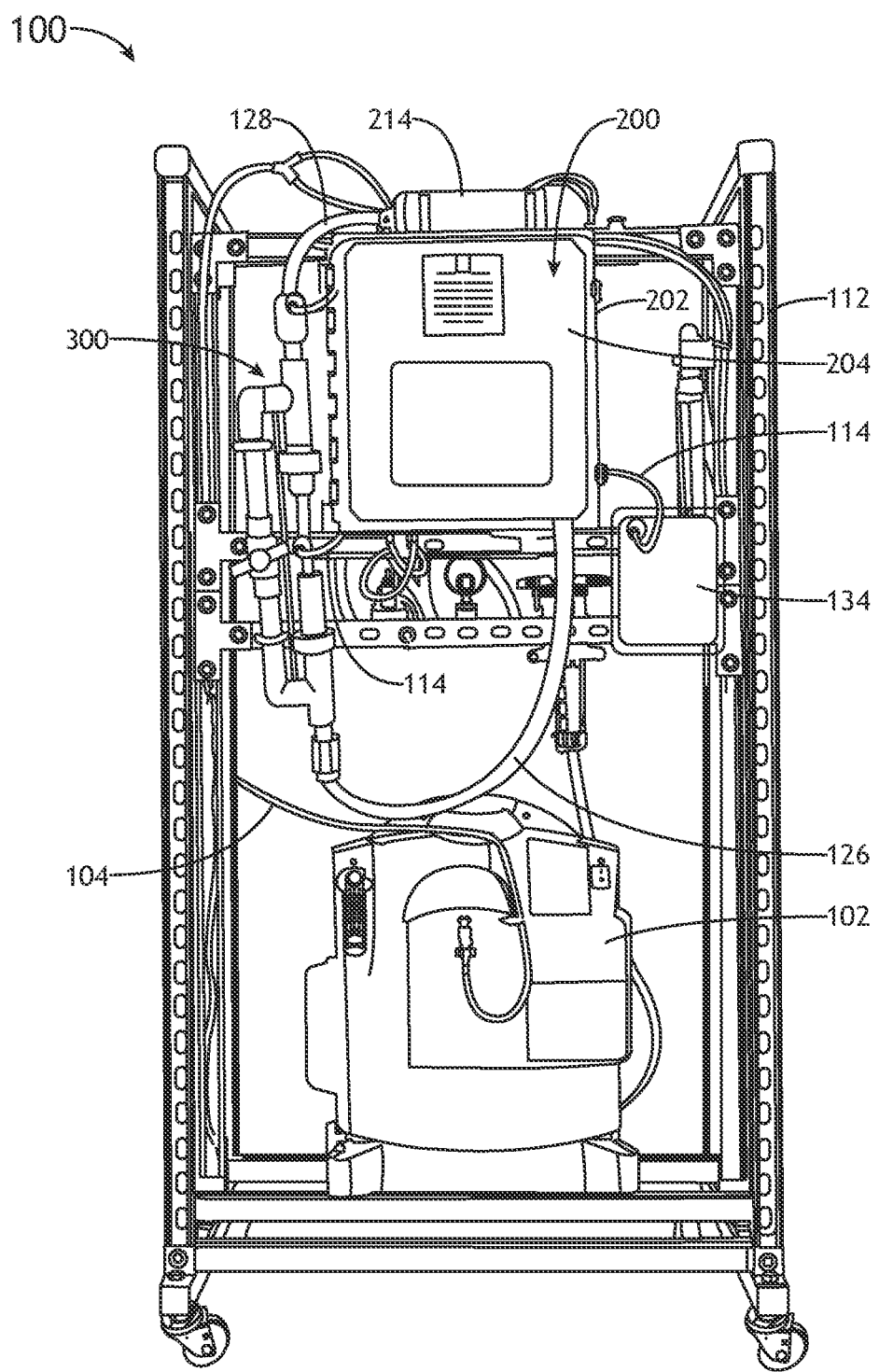
FIG. 1A is a front view of a system for creating an oxidation reduction potential (ORP) in water, in accordance with one or more embodiments of this disclosure.

Reference will now be made in detail to the subject matter disclosed, which is illustrated in the accompanying drawings.

Embodiments of this disclosure are directed to systems for creating an oxidation reduction potential (ORP) in water using one or more pipe assembly for in-line mixing of water and ozone solution. In residential or commercial applications, the system may be configured to supply ozonated water to one or more taps that receive water from a main water source (e.g., the main water line). In this regard, the system can be employed as a whole home or building water cleansing, disinfecting, and/or softening solution. Alternatively, the system may be used for a particular zone of a residential or commercial building. In some cases, a plurality of systems can be used to ozonate water in a plurality of zones within a residential or commercial building. The system can also be used for cleansing and/or degreasing hard surfaces such as plastic, glass, ceramic, porcelain, stainless steel, or the like. The system can also be used for cleansing and/or degreasing equipment such as food service equipment which may include, but are not limited to, ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, and grease traps. The system can also be used for cleansing and/or degreasing HVAC or plumbing systems such as roof top units, air scrubbers, humidifiers, water heaters, pumps, or the like.

An ORP value can be used for water system monitoring to reflect the antimicrobial potential of a given sample of water. ORP is measured in millivolts (mV), with typically no correction for solution temperature, where a positive voltage shows a solution attracting electrons (e.g., an oxidizing agent). For instance, chlorinated water will show a positive ORP value whereas sodium sulfite (a reducing agent) loses electrons and will show a negative ORP value. Similar to pH, ORP is not a measurement of concentration directly, but rather of activity level. In a solution of only one active component, ORP indicates concentration. The World Health Organization (WHO) adopted an ORP standard for drinking water disinfection of 650 millivolts. That is, the WHO stated that when the oxidation-reduction potential in a body of water measures 650 (about ⅔ of a volt), the sanitizer in the water is active enough to destroy harmful organisms almost instantaneously. For example, *E. coli, Salmonella, Listeria*, and Staph pathogens have survival times of under 30 seconds when the ORP is above 650 mV, compared against >300 seconds when it is below 485 mV.

An example ORP sensor uses a small platinum surface to accumulate charge without reacting chemically. That charge is measured relative to the solution, so the solution "ground"

voltage comes from the reference junction. For example, an ORP probe can be considered a millivolt meter, measuring the voltage across a circuit formed by a reference electrode constructed of silver wire (in effect, the negative pole of the circuit), and a measuring electrode constructed of a platinum band (the positive pole), with the water in-between.

Increasingly, microbial issues are commanding the attention of water treatment operators, regulators, media, and consumers. There are many treatment options to eliminate pathogenic microbes from drinking water. One such option includes ozone ($O_3$), an oxidizing agent approved for drinking water treatment by the U.S. Environmental Protection Agency. For instance, ozone is one of the strongest disinfectants approved for potable water treatment capable of inactivating bacteria, viruses, *Giardia*, and *Cryptosporidium*.

The disclosed system may be configured to output water having an ORP of about 600 mV to about 1000 mV, with particular embodiments being configured to output water having an ORP of about 700 mV to about 900 mV to provide pathogenic control. Additionally, the system may be configured to reduce the surface tension of the water being used to cleanse and/or degrease hard surfaces and equipment by creating a water and ozone solution wherein the surface tension of the water is reduced from about 72 Millinewtons per meter at 20 degrees Centigrade to about 48-58 Millinewtons per meter at 20 degrees Centigrade to greatly improve the cleansing and/or degreasing qualities thereof.

In embodiments, the system employs a pipe assembly for in-line mixing of water and ozone solution. Through the use of a pipe assembly that is structurally separate from an ozone supply unit, the system is able to handle high pressure water flow through the pipe assembly without fear of a leak causing damage to electronic components associated with the ozone supply unit (e.g., ozone generators, controllers, relays, etc.). Furthermore, the pipe assembly may be linearly disposed within the water supply framework of a residential/commercial building for improved throughput with a reduced footprint.

Figure 1B:
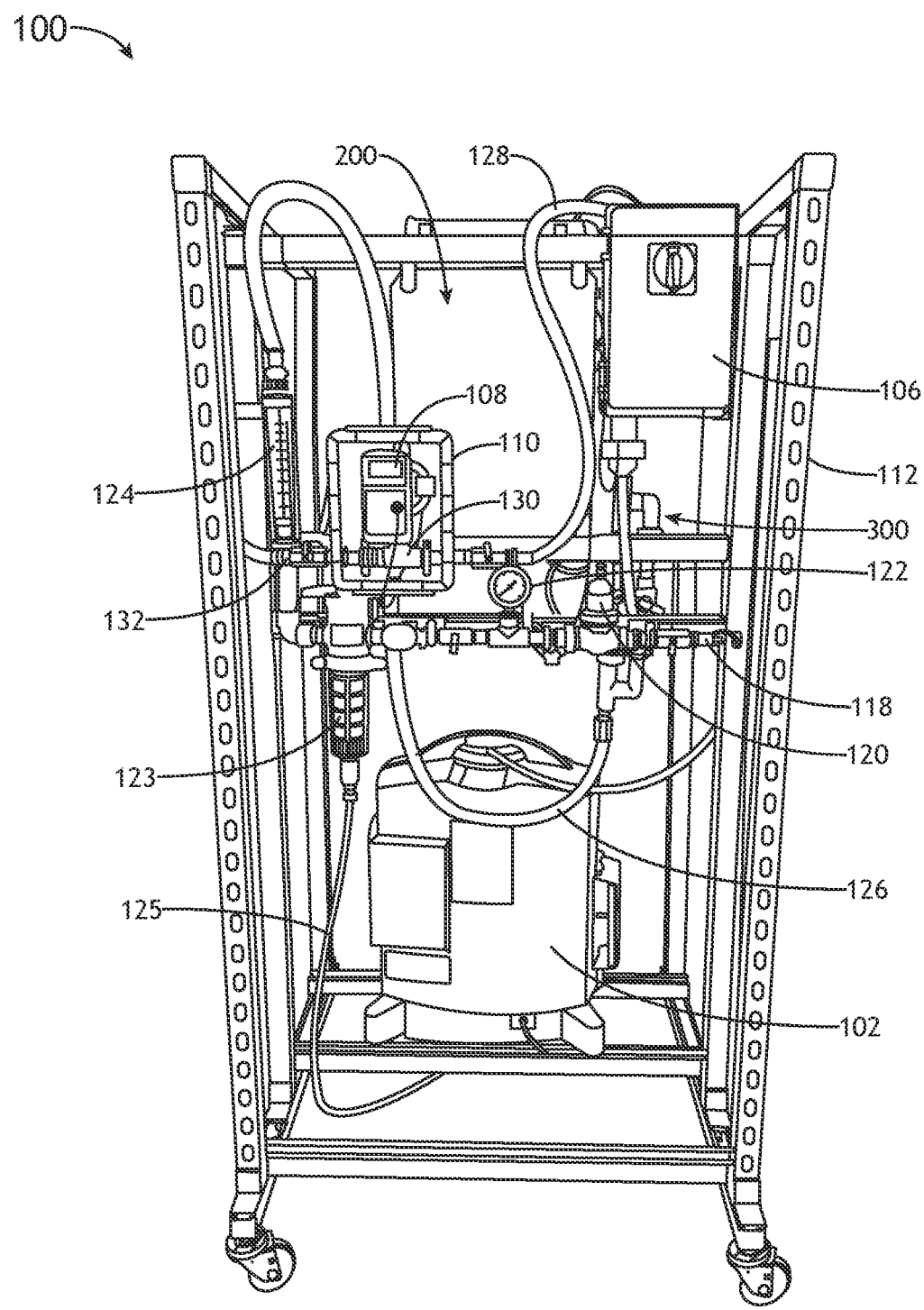
FIG. 1B is a rear view of the system for creating an oxidation reduction potential (ORP) in water, in accordance with one or more embodiments of this disclosure.

FIGS. 1A and 1B illustrate a system 100 for creating an ORP in water, in accordance with one or more embodiments of this disclosure. The system 100 includes an ozone supply unit 200 configured to output ozone for creating an ORP in water and a pipe assembly 300 for in-line mixing of the ozone into the water in order to output a water and ozone solution. Although the system 100 is discussed with regard to applications that employ water to generate a water and ozone solution, it is contemplated that the system 100 may be configured to generate other types of ozonated fluid solutions for the purposes of cleansing, degreasing, decontaminating, and/or fluid treatment.

As shown in FIG. 1A, the ozone supply unit 200 may include a supply unit enclosure 202. In embodiments, the supply unit enclosure 202 and the pipe assembly 300 are independently locatable, separate structures. While the supply unit enclosure 202 and pipe assembly 300 are separate and capable of being disposed at a distance from one another, the supply unit enclosure 202 and the pipe assembly 300 are still fluidically coupled by one or more tubes 114 (e.g., flexible tubing, pipes, etc.) for transferring ozone from the ozone supply unit 200 to the pipe assembly 300. As shown in FIG. 3C, the ozone supply unit 200 and the pipe assembly 300 may also be communicatively coupled by one or more connectors 116 (e.g., wires, cables, optical fibers, etc.) for transmitting signals between the ozone supply unit 200 and the pipe assembly 300. In other embodiments, the ozone supply unit 200 and the pipe assembly 300 may include wireless communication interfaces (e.g., wireless receivers, transmitters, and/or transceivers) for sending signals from one device to the other.

The supply unit enclosure 202 may have a securable lid/cover 204 that can enclose (e.g., when secured/closed) and provide access to (e.g., when removed/opened) the components housed in an interior portion of the supply unit enclosure 202. As shown in FIG. 1A, the securable lid/cover 204 may be secured to the supply unit enclosure 202 by a hinge on one side and a latch or fastener on an opposing side. In other embodiments, the securable lid/cover 204 may be a sliding cover or may be secured to the supply unit enclosure 202 by one or more fasteners (e.g., screws to mate with bores in the supply unit enclosure 202, latches, interference fit fasteners, clipping fasteners, magnetic fasteners, or the like). The supply unit enclosure 202 may further include coupling portions to couple with a power source, a switch to engage or disengage power to the ozone supply unit 200/system 100, an indicator (e.g., a light source), any combination thereof, and so forth.

Figure 2:
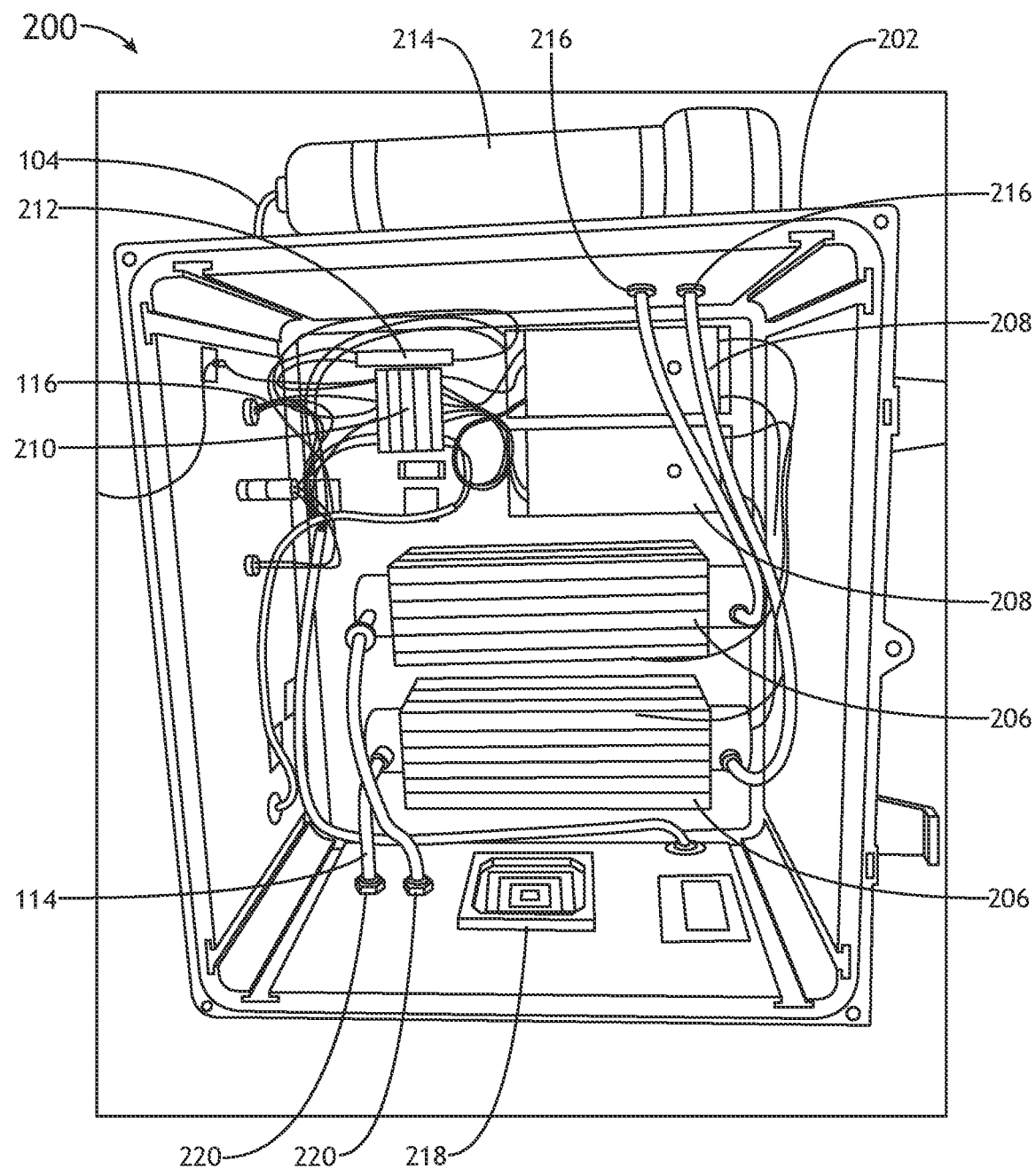
FIG. 2 is a perspective view of an open ozone supply unit of the system for creating an oxidation reduction potential (ORP) in water, in accordance with one or more embodiments of this disclosure.

FIG. 2 illustrates the ozone supply unit 200 with the lid/cover 204 removed from the supply unit enclosure 202, in accordance with one or more embodiments of this disclosure. As shown in FIG. 2, the supply unit enclosure 202 includes one or more air intake ports 216 and one or more ozone output ports 220. The ozone supply unit 200 includes a plurality of ozone generators 206 (e.g., two or more generators 206) disposed within the supply unit enclosure 202. The ozone generators 206 are fluidically coupled to the one or more air intake ports 216 and the one or more ozone output ports 220 of the supply unit enclosure 202. One or more controllers 208 are also disposed within the supply unit enclosure 202. The one or more controllers 208 are communicatively coupled to the ozone generators 206.

In embodiments, each of the ozone generators 206 may include a corona discharge tube configured to use oxygen supplied via the one or more air intake ports 216 to generate ozone, such as through splitting of oxygen molecules in the air through electrical discharge caused by supplying power to a dielectric material within the corona discharge tube. For example, each ozone generator 206 may include an input port that is fluidically coupled to an air intake port 216 and configured to convert oxygen from incoming air into ozone. The ozone generators 206 may be powered by a power source 212 (e.g., a 120V/240V power supply unit). A power signal from power source 212 may be transformed via a transformer suitable for applying the voltage to the dielectric within the corona discharge tube of the ozone generator 206. For example, a transformer may be coupled to or integrated within a controller 208 for each ozone generator 206 or one controller 208 that controls a plurality of ozone generators 206. In some embodiments, each controller 208 includes a logic circuit (e.g., processor) that is programmed to selectively activate or deactivate one or more connected ozone generators 206. In other embodiments, each controller 208 is a transformer that passively activates one or more connected ozone generators 206 when power is supplied to the controller 208 and deactivates the one or more connected ozone generators 206 when the controller 208 is disconnected from power. The ozone supply unit 200 may include a relay 210 (e.g., a switchboard with analog or digital logic circuits) that controls distribution of power and/or communication signals withing the ozone supply unit 200. For example, the relay 210 may be connected to power source 212, power switch 106, an indicator, one or more controllers 208 and/or ozone generators 206, and any sensors/switches (e.g., flow switch 322) of the system.

In some embodiments, the ozone generators 206 may be operated at 110 volts/60 Hz and have an operating frequency of about 450 KHz and 550 KHz, with a power rating of less than about 15 watts, and with a unit performance for electrical consumption of about 32 watts. For example, the ozone generators 206 may have an operating frequency of about 480 KHz. Further, the ozone generators 206 can be provided according to ISO 9001 CE standards.

Each of the ozone generators 206 may be configured to produce from about 800 mg ozone per hour to about 1200 mg ozone per hour, although other ranges may be appropriate depending on the application. In some embodiments, each of the ozone generators 206 produces about 1000 mg ozone per hour. The ozone generators 206 may include other methods and systems for generating ozone, including but not limited to, electrochemical cells configured to generate ozone from water by placing an anode and a cathode in contact with opposite sides of a proton exchange membrane (PEM), and supplying power to the cell, whereby water flowing over the surface of the anode breaks down into hydrogen atoms and oxygen atoms that assemble to form $O_3$ (ozone).

In embodiments, each ozone supply unit 200 may further include an air dryer 214 (or filter), which may be externally coupled to the supply unit enclosure 202. The air dryer 214 is configured to remove moisture from air before the air is supplied to the ozone generators 206 through the one or more air intake ports 216. The air dryer 214 may be configured to dry the air to a minus dew point by removing water vapor or moisture therefrom, where the water could inhibit the production of ozone by the ozone generators 206.

In some embodiments, the air dryer 214 includes or is coupled to an air compressor. The pressure provided by the compressor can vary depending on the water pressure supplied to the system 100, where the pressure applied by the compressor can be balanced based on the flow rate of air received by the ozone generators 206 via the one or more air intake ports 216 and the water pressure supplied to the system 100 to obtain a particular ORP of the water. For example, the compressor may be configured to compress the filtered air at least about 15 KPa (e.g., more particularly at a pressure of 18 KPa or about 2.6 psi) to provide a gas throughput in each ozone generator 206 of about 8 SCFH (standard cubic feet per hour), where the water pressure in each fluid path is about 25 psi to 100 psi (e.g., a reasonable rating for many residential and commercial facilities), to provide an ORP in the water at the water output port of at least about 600 mV (e.g., about 600 mV to about 1000 mV, more particularly about 700 to 900 mV). At these pressures, each ozone generators 206 has a residence time of the gas of about three seconds. The pressure applied by the compressor can affect the rate at which the gas flows through an ozone generator 206, which can affect contact time of the air with the components of the ozone generator 206, which can also affect mass gas transfer rates within the ozone generator 206.

In embodiments, the ozone supply unit 200 includes a plurality of ozone generators 206. For example, in an embodiment illustrated FIG. 2, the ozone supply unit 200 includes two ozone generators 206. Each ozone generator 206 may be coupled to a respective air intake port 216 and ozone output port 220. However, in some embodiments, two or more ozone generators 206 may be fluidically connected in parallel between an air intake port 216 and an ozone output port 220. For example, splitters/combiners can be used to fluidically couple each pair/set of ozone generators 206 in parallel. The ozone supply unit 200 may additionally/alternatively include two or more ozone generators 206 connected in series with one other. Such configurations provide one or more backup ozone generators 206 in case of malfunction or inoperability of one or more of the other ozone generators 206. On average, each ozone generator 206 may have an operating life of about 10,000 working hours.

In some embodiments, the supply unit enclosure 202 also includes a vent 218 (e.g., an exhaust vent) to bring cool air into the supply unit enclosure 202 and/or remove hot air from the supply unit enclosure 202. The vent 218 may be equipped with a fan to further facilitate airflow.

Although FIG. 2 illustrates one ozone supply unit 200, it is understood that any other ozone supply units 200 in the system 100 may be identically or similarly structured. In this regard, any components or configurations described with regard to the ozone supply unit 200 in FIG. 2 are applicable to all of the ozone supply units 200 in the system 100.

Figure 3A:
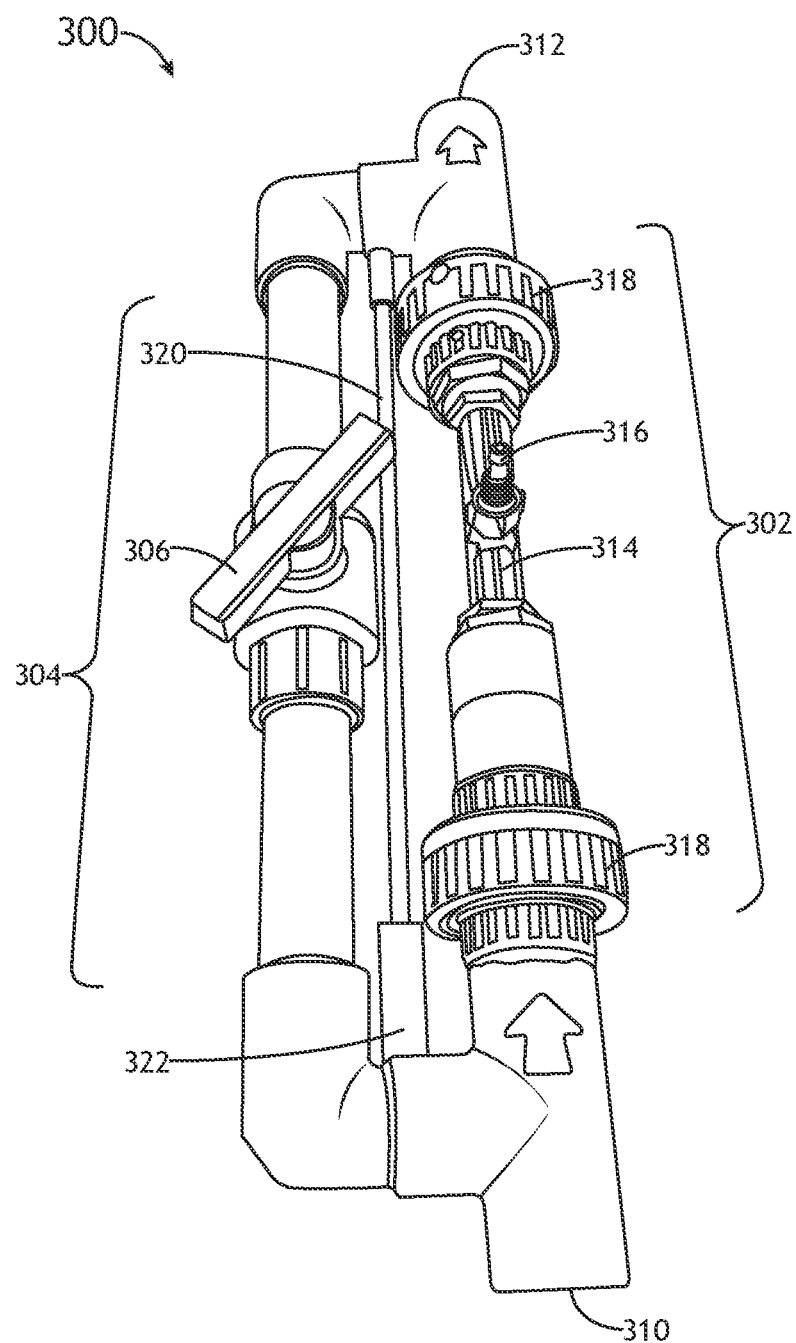
FIG. 3A is a perspective view of a pipe assembly of the system for creating an oxidation reduction potential (ORP) in water, in accordance with one or more embodiments of this disclosure.
Figure 3B:
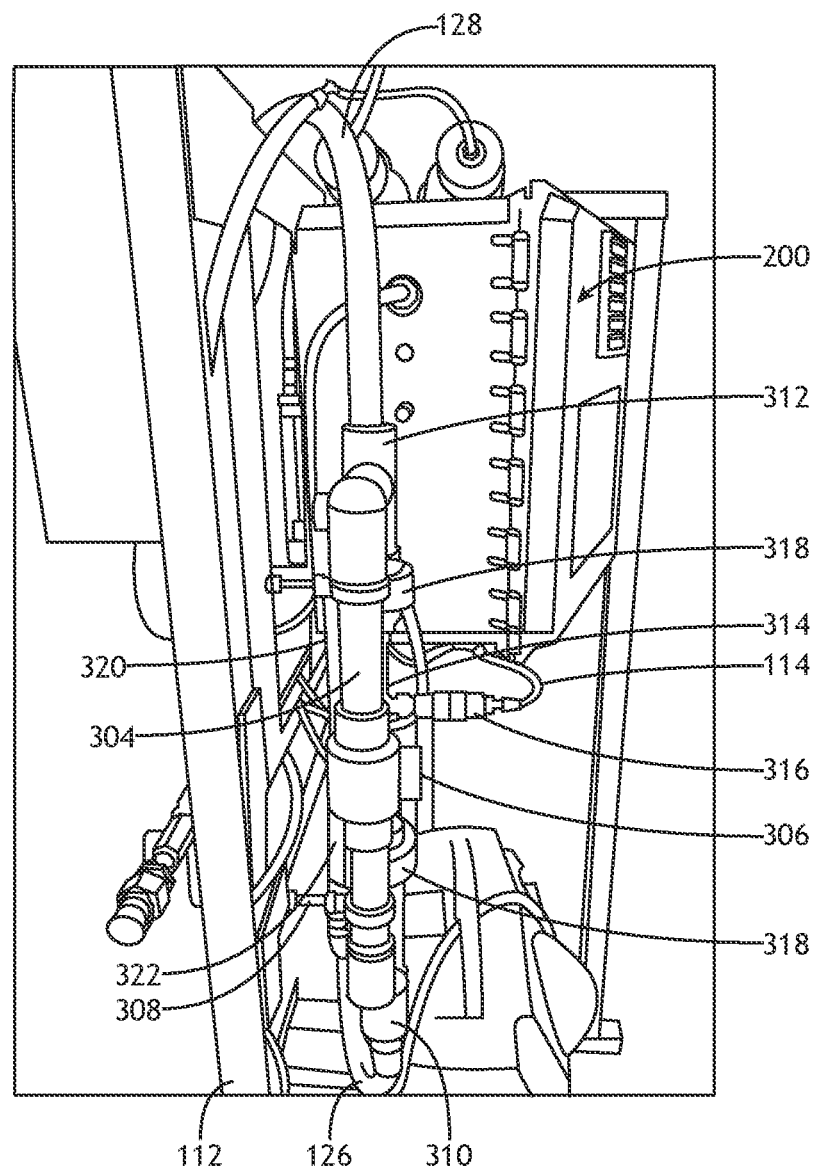
FIG. 3B is a zoomed-in partial side view of the system for creating an oxidation reduction potential (ORP) in water, in accordance with one or more embodiments of this disclosure.
Figure 3C:
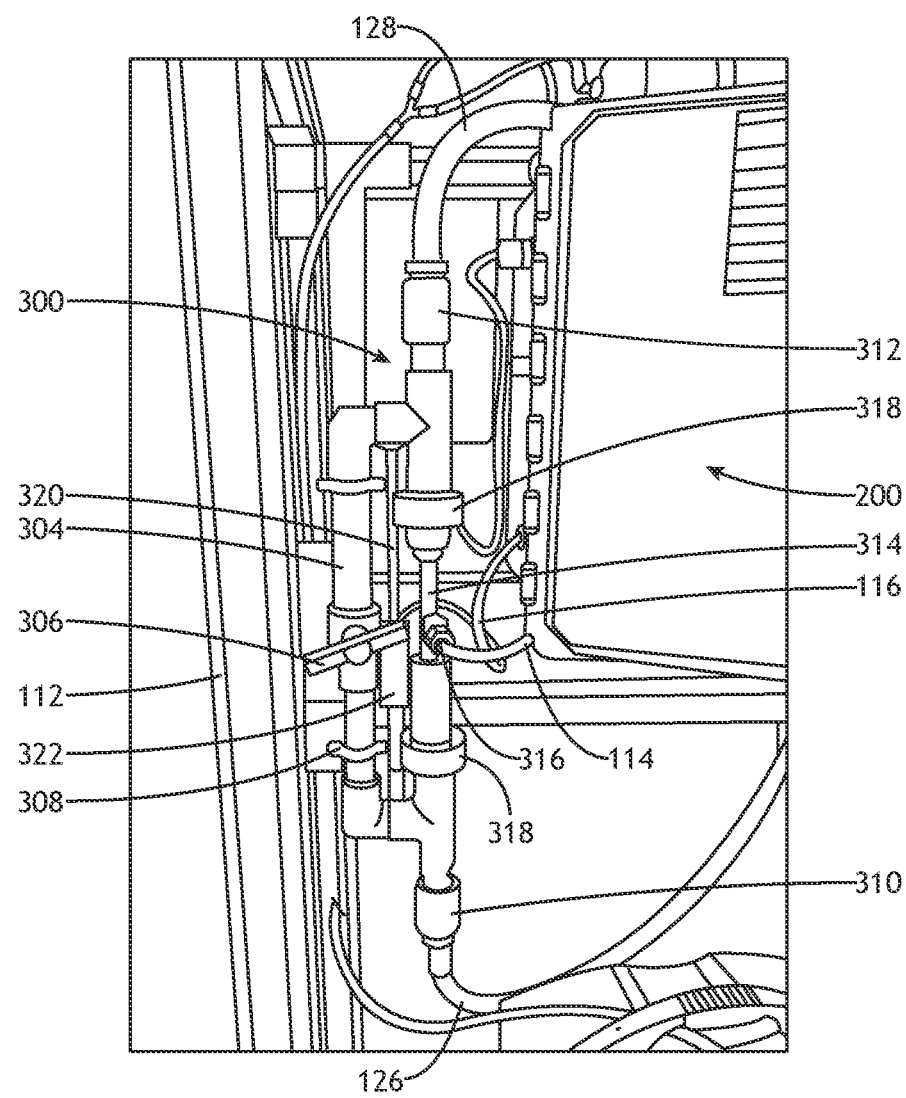
FIG. 3C is a zoomed-in partial front view of the system for creating an oxidation reduction potential (ORP) in water, in accordance with one or more embodiments of this disclosure.

FIGS. 3A through 3C illustrates the pipe assembly 300, in accordance with one or more embodiments of this disclosure. As shown in FIG. 3A, the pipe assembly 300 includes a first flow path 302 for water to flow through. The first flow path 302 may include one or more pipe segments and/or fittings that define a first fluid pathway between a water input port 310 and a water output port 312 of the pipe assembly 300. The first flow path 302 includes one or more ozone intake ports 316 that are fluidically coupled to the one or more ozone output ports 220 of the supply unit enclosure 202. In embodiments, one or more ozone intake ports 316 of the pipe assembly 300 are fluidically coupled to the one or more ozone output ports 220 of the ozone supply unit 200 by one or more tubes 114 (e.g., flexible tubing, pipes, etc.) for transferring ozone from the ozone supply unit 200 to the pipe assembly 300. As shown in FIG. 1A, in some embodiments, the system 100 may further include a solenoid valve 134 configured to purge residual ozone from the one or more tubes 114 in between uses (e.g., when the system 100 starts up, shuts down, or transitions between active/inactive modes). For example, the solenoid valve 134 may be configured to receive a control signal from the relay 210 to indicate startup, shutdown, and/or ozone generator activity/inactivity, wherein the control signal triggers the solenoid valve to purge any leftover ozone from the one or more tubes 114. This avoids excessive ozone in the tubes 114 when the ozone generators 206 are activated as the presence of too much ozone in the tubes 114 may cause an unsafe condition, such as a fire/explosion, component damage, or ozone leak.

The pipe assembly 300 further includes a second flow path 304 fluidically coupled in parallel with the first flow path 302. For example, the second flow path 304 includes one or more pipe segments and/or fittings that define a second fluid pathway in parallel with the first fluid pathway (first flow path 302) between the water input port 310 and the water output port 312 of the pipe assembly 300. The second flow path 304 may form a D or P shaped branch out of the first flow path 302. This structural arrangement may help maintain more water flow through the first flow path 302 than the second flow path 304.

The second flow path 304 includes a control valve 306 that is configured to selectively permit (or restrict) water flow through the second flow path 304. When the control valve 306 is opened to permit a portion of the water to flow through the second flow path 304, the fluid action produces a negative pressure in the first flow path 302. The negative pressure then causes ozone from the ozone supply unit 200 to be drawn into the first flow path 302 through the one or more ozone intake ports 316 and mixed into the water flowing through the first flow path 302. In some embodiments, the control valve 306 is adjustable to vary the negative pressure produced in the first flow path 302 in order to control an ozone concentration of the water and ozone solution output by the system. For example, the control valve 306 may be adjustable to control the flow rate of water through the second flow path 304 in order to increase/decrease suction through the one or more ozone intake ports 316. In some embodiments, the level of suction (and hence the ozone concentration of the resulting aqueous ozone solution) can be increased by increasing the flow rate of water through the second flow path 304; and similarly, the level of suction (and hence the ozone concentration of the resulting aqueous ozone solution) may be reduced by decreasing the flow rate of water through the second flow path 304. Some configurations may be reversed such that the level of suction (and hence the ozone concentration of the resulting aqueous ozone solution) can be increased by decreasing the flow rate of water through the second flow path 304, and the level of suction (and hence the ozone concentration of the resulting aqueous ozone solution) may be reduced by increasing the flow rate of water through the second flow path 304.

Figure 4:
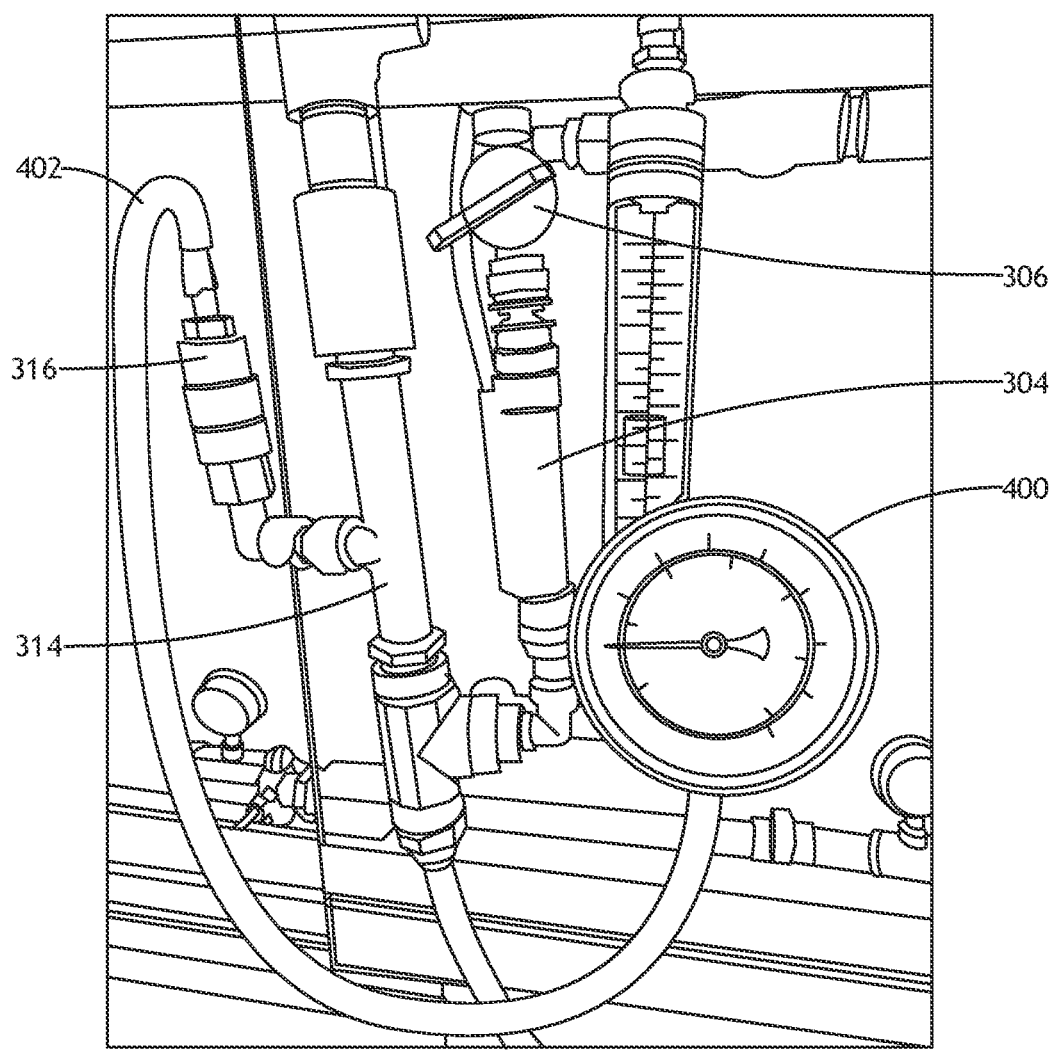
FIG. 4 is a zoomed-in partial front view of the system for creating an oxidation reduction potential (ORP) in water, wherein a pressure gauge is coupled to an ozone intake port of the pipe assembly to calibrate/set a suction force (i.e., negative pressure) in a first flow path of the pipe assembly by adjusting a control valve that selectively permits water to flow through a second flow path that is in parallel with the first flow path, in accordance with one or more embodiments of this disclosure.

As shown in FIG. 4, to calibrate/set the suction force of the one or more ozone intake ports 316, a pressure gauge 400 can be coupled to an ozone intake port 316 of the pipe assembly 300 (e.g., directly or by one or more tubes 402). The suction force (i.e., negative pressure) in the first flow path 302 of the pipe assembly 300 can be set/calibrated by adjusting the control valve 306 that selectively permits water to flow through the second flow path 304 until the negative pressure reaches a selected value or is within an appropriate range to achieve the required suction force for the ozone concentration and flow rate requirements of the system.

In embodiments, the first flow path 302 includes fluid mixer 314 that is coupled to or integrated within the first flow path 302. For example, the fluid mixer 314 may be removably coupled between two pipe fittings 318 to allow for easy removal or replacement of the fluid mixer 314 if needed. The fluid mixer 314 may be configured to introduce/inject ozone generated by the ozone generators 206 into the water flowing through the first flow path 302. For example, the fluid mixer 314 may include and/or may be fluidically coupled to the ozone intake port 316 and configured to inject at least a portion of the ozone received via the ozone intake port 316 into the water flowing through the first flow path 302.

The fluid mixer 314 may be a multi-port coupler including a water inlet, a water outlet, and an ozone input port (e.g., ozone intake port 316). The multi-port coupler may simply be pipe/tube fittings with an ozone input port (e.g., ozone intake port 316) formed therein, 3-way pipe/tube fittings, or the like.

In some embodiments, the multi-port coupler includes a venturi. A venturi can include an injector venturi design (e.g., a "T" design), where the venturi is coupled between the water inlet and the water outlet, and where ozone is introduced to the venturi through another port (i.e., the ozone input port) positioned perpendicular to the flow path of the water (from the water inlet to the water outlet). During operation, ozone generated by the ozone generators 206 is drawn into the venturi and mixed with the water stream flowing from the water inlet to the water outlet. A pressure differential between the water inlet and the water outlet may serve to facilitate drawing the ozone into the venturi and to facilitate mixing of the ozone and the water. In some embodiments, a pressure differential greater than 20 psi inlet over outlet (e.g., at least a 20 psi difference between the water inlet and the water outlet, with pressure higher at the water inlet) is provided to generate negative suction in the venturi to thereby draw in the generated ozone, while assuring the energy for water flow and pressure for operation of the venturi.

In order to further increase effectiveness of the mixing process delivered by the venturi, the water and ozone solution may pass through an in-line mixer coupled between the venturi and the water outlet. In this regard, the fluid mixer 314 may include a combination of a venture and an in-line mixer, or another type of multi-port coupler with an in-line mixer. The in-line mixer can facilitate further breaking or mixing of ozone bubbles already introduced to the water to generate a mixture (or solution) of water and substantially uniform-sized ozone bubbles. The small uniform-size ozone bubbles can adhere to each other to lower the surface tension of the water and ozone solution. For example, water can have a surface tension of about 72 Millinewtons, whereas the solution of water and substantially uniform-sized ozone bubbles can have a surface tension of about 48-58 Millinewtons. In embodiments, the in-line mixer has an internal diameter that equals an internal diameter of the output port of the venturi to which the in-line mixer is coupled. The same internal diameter can provide an uninterrupted transition of the fluid flowing from the venturi to the in-line mixer, such as to maintain a vortex action or mixing action of the water and the ozone bubbles. The in-line mixer also provides increased contact time between the water and ozone bubbles and can facilitate preparation of uniform ozone bubble size. In some embodiments, the in-line mixer has a length of about two inches downstream from the venturi, which can allow sufficient time for the velocity of the vortex action caused by the pressure differential of the venturi to crush the gaseous bubbles entrained in the solution into uniformed size bubbles. The in-line mixer can also reintroduce undissolved gas back into the solution resulting in increased efficiency as well as reduced off-gas at the point of application. The in-line mixer can include multiple chambers through which the water and ozone solution flows. The size of the chambers can be determined based on the water flow (e.g., throughput), gas mixing, and desired time exposure. In some embodiments, operation of the system 100 produces a water stream at the water output port having a molar concentration of ozone of at least 20%, or more particularly at least 25%, far surpassing previous systems that have mass gas transfer rates of less than 10%.

The ozone supply unit 200 is communicatively coupled to a flow switch 322 configured to detect water flow through the system 100. As shown in FIGS. 3A through 3C, the flow switch 322 may be integrated within or coupled to the pipe assembly 300. For example, the flow switch 322 may be fluidically coupled to a third flow path 320 that is in parallel with the first and second flow paths 302 and 304 of the pipe assembly 300. In other embodiments, the flow switch 322 may be disposed within the supply unit enclosure 202 or coupled to any other the fluid path for water flow through the system 100 (e.g., water input line 126, water output line 128, flow path 302, flow path 304, etc.).

The flow switch 322 can be configured to provide electric signals indicative of water flow through the system 100 (e.g., by sensing flow through flow path 320, or another fluid pathway in alternative embodiments). For example, the flow switch 322 may be a mechanical flow switch/sensor, electromagnetic flow switch/sensor, pressure-based flow switch/sensor, optical flow switch/sensor, or the like, configured to provide an electric signal indicative of a flow of fluid (e.g., water) through the system 100. In some embodiments, the flow switch 322 may be a solenoid-based flow switch/ sensor, such as to avoid significant restriction of flow through the system 100.

In embodiments, the flow switch 322 is configured to transmit one or more control signals to the one or more controllers 208 in response to sensing a flow of water through the system 100 (e.g., by sensing flow through flow path 320, or another fluid pathway in alternative embodiments). In response to receiving the one or more control signals, the one or more controllers 208 are configured to cause the ozone generators 206 to generate ozone. In some embodiments, the controllers 208 are transformers that become activated by control signals (e.g., status/power signals) transmitted by the flow switch 322 in response to sensing a flow of water through the fluid paths. In other embodiments, the controllers 208 may further include microprocessors, microcontrollers, or other programmable logic devices. In such embodiments, the one or more controllers 208 may be configured (e.g., programmed) to activate the transformers and/or ozone generators 206 in response to the control signals (e.g., status signals) and possibly based on other sensor signals being monitored by the one or more controllers 208.

The flow switch 322 may be communicatively coupled to the one or more controllers 208 by one or more connectors 116 (e.g., wires, cables, optical fibers, etc.) for transmitting signals between the flow switch 322 and the one or more controllers 208 For example, as shown in FIG. 2, the one or more connectors 116 may be coupled to a relay 210 the ozone supply unit enclosure 202. In other embodiments, the ozone supply unit 200 may include a wireless communication interface (e.g., wireless receivers, transmitters, and/or transceivers) for receiving signals from the flow switch 322.

As discussed above, the ozone supply unit 200 may include a relay 210 that distributes the incoming signals to the one or more controllers 208. In embodiments, the flow switch 322 is communicatively coupled to the relay 210 by the one or more connectors 116. The relay 210 may be configured to transmit the control signals from the flow switch 322 to the controllers 208, whereby the controllers 208 are programmed to activate the ozone generators 206 in response to receiving one or more control signals indicating a flow of water through the system. Alternatively, the relay 210 itself may be configured to connect the controllers/ transformers 208 to power (or to directly power the ozone generators 206 if no controllers/transformers 208 are present) in response to receiving one or more control signals indicating a flow of water through the system 100. In further embodiments, the ozone supply unit 200 may include a wireless communication interface (e.g., wireless receivers, transmitters, and/or transceivers) for receiving signals from the flow switch 322. For example, the flow switch 322 and one or more of the controllers 208 and/or relay 210 may include wireless communication interfaces for sending/receiving wireless communication/control signals.

In some embodiments, the system 100 includes multiple flow switches 322 to provide redundancy and/or status indications for monitored fluid paths in order to detect faults (e.g., a faulty sensor, a clogged or disconnected fluid path, or the like). In some embodiments, the ozone generators 206 may be shut off when a fault is detected.

Although FIGS. 3A through 3C illustrates pipe assembly 300, it is understood that any other pipe assembly 300 in the system 100 may be identically or similarly structured. In this regard, any components or configurations described with regard to the pipe assembly 300 in FIGS. 3A through 3C are applicable to all of the pipe assemblies 300 in the system 100.

Referring again to FIGS. 1A and 1B, the system 100 may further include one or more oxygen concentrators 102 configured to supply oxygen-enriched air to the one or more air intake ports 216 of the ozone supply unit 200. In embodiments, the oxygen concentrator 102 is configured to direct the oxygen-enriched air through the air dryer 214. The oxygen concentrator 102 may also remove moisture from the air. In this regard, the incoming air may undergo two drying stages. The oxygen concentrator 102 may be fluidically coupled to the ozone supply unit 200 (e.g., to the air dryer 214 and/or air intake port 216) by one or more tubes 104 (e.g., flexible tubing, pipes, etc.) for transferring oxygen-enriched air from the oxygen concentrator 102 to the ozone supply unit 200.

In embodiments, the system 100 may further include one or more ORP monitors 108 configured to detect an ORP of the water flowing through the plurality of fluid paths. For example, as shown in FIG. 1B, the system 100 may include an ORP sensor 130 for detecting an ORP of the water and ozone solution being dispensed from an outlet 132 of the system 100. The system 100 may include a transportable support frame 112 configured to support various components of the system 100 (e.g., the ozone concentrator 102, ozone supply unit 200, pipe assembly 300, and various electronics and fluid paths). For example, the ozone supply unit 200 and the pipe assembly 300 may be mounted to the transportable support frame 112 by fasteners (e.g., screws, bolts, hooks, straps, etc.), brackets 308, or the like. The transportable support frame 112 may be a wheeled frame capable of transporting the system 100 from one place to another. For example, the transportable support frame 112 may be supported by a plurality of wheels, casters, or the like. In some embodiments, the system 100 includes a main power switch 106 configured to connect or disconnect power to all of the system components. The main power switch 106 may be mounted to the transportable support frame 112. As shown in FIG. 1A, a front side of the transportable support frame 112 may also include one or more holsters 110 configured to hold the one or more ORP monitors 108. Referring now to FIG. 1B, a backside of the transportable support frame 112 may support fluid paths for connecting the system 100 to an input (e.g., a water source) and an output (e.g., equipment). For example, an input path may include, but is not limited to, an inlet 118, one or more pressure regulators 120, a pressure gauge 122, a flow rate indicator 124, and one or more input lines 126 for directing the water into the pipe assembly 300. In embodiments, the input path may further include a sediment filter 123 configured to remove solids from the input water. In some embodiments, the sediment filter 123 may be configured to dispose of the solids through a waste tube 125. An output path may include, but is not limited to, one or more output lines 128 for directing water and ozone solution out of pipe assembly 300, one or more ORP sensors 130, and outlet 132.

The ozone supply unit 200 may be configured to supply ozone to the pipe assembly 300 at a rate of about 5 liters/min. In turn, the system 100 may be configured to dispense water and ozone solution at a rate of about 5 gal/min and can treat water having inlet pressures of between 50 psi and 100 psi to provide water having an ORP of between 600 mV and 1000 mV to provide pathogenic control without introduction of harsh treatment chemicals, such as chlorine. After operation of the system 100, the output water and ozone solution can provide removal of organic and inorganic compounds, can provide removal of micro-pollutants (e.g., pesticides), can provide enhancement of the flocculation/coagulation decantation process, can provide enhanced disinfection while reducing disinfection by-products, can provide odor and taste elimination of the treated water, and so forth. The solubility of ozone in water is quite good, about 10 to 15 times greater than for oxygen under normal drinking water treatment conditions. About 0.1 to 0.6 liters of ozone will dissolve in one liter of water. The size of the ozone gas bubble in the system 100 can influence gas transfer characteristics. In some embodiments, the fluid mixer 314 generate an ozone bubble size of about 2 to about 3 microns. For instance, micro-bubbles can be produced fluid mixer 314 and/or sheared into uniformed micro-size bubbles as the solution passes through flow path 302.

Corona discharge ozone can be used virtually anywhere, such as with portable versions of the system 100. Since ozone is made on site, as needed and where needed, there is no need to ship, store, handle or dispose of it, nor any containers associated with shipping, storing, handling, and disposing a treatment chemical, as is the situation with most chemicals utilized in water treatment.

The system 100 may be configured to provide indications pertaining to the operation status of the system 100, such as to ensure proper operation, or to provide an indication regarding a need for adjustment, servicing, or maintenance. For example, the flow switch 322 may be configured to send the signal to at least one indicator that provides a visual, tactile, or audible indication that the fluid (e.g., water) is flowing through the fluid paths in the pipe assembly 300. In some embodiments, the indicator is a light source (e.g., an LED) configured to illuminate upon receiving a signal from the flow switch 322. The indicator may also be coupled to a sensor (e.g., a relay) configured to measure that a voltage is applied to an ozone generator 206. When a proper voltage is applied to the ozone generator 206, the sensor can send a signal to the indicator. In some embodiments, the indicator will provide a visual, tactile, or audible indication when each sensor and the flow switch 322 provide their respective signals to the indicator. For example, the system 100 can include a relay 210 coupled to the power source 212 and the flow switch 322. The relay 210 may be configured to send an activation signal to the indicator when the power source 212 is providing power to the ozone generators 206 and when the flow switch 322 provide signals regarding fluid flow through the system 100. In such a configuration, the indicator can verify that the system 100 is operating under design conditions (e.g., having an active flow of water, and having a sufficient power supply to the ozone generators 206).

In some embodiments, the system 100 may include an in-line ORP meter (e.g., ORP sensor 130 and monitor 108) positioned to measure the ORP of the water and ozone solution, such as adjacent a water output port, coupled within a distribution line, or the like. The in-line ORP meter can be coupled with the relay 210, such that the in-line ORP meter provides a signal to the relay 210 upon detection of a desired ORP or range of ORPs (e.g., in the range of 600 to 1000 mV, or other predetermined range). The relay 210 can then provide an activation signal to an indicator upon proper functioning of the system 100 (e.g., when the power source 212 is providing power to the ozone generators 206, when the flow switch 322 provide signals regarding fluid flow through the system 100, and when the in-line ORP meter detects a desired ORP of the water and ozone solution generated by the system 100). When the indicator is not activated, this can provide an indication that a component or components of the system 100 may need adjustment, servicing, or maintenance. Alternatively, the system 100 can be configured to activate an indicator upon failure of one or more of the components of the system 100 (e.g., no power supplied to the ozone generators 206, no flow of water detected by the flow switch 322, or an out-of-range ORP detected by the in-line ORP meter).

By providing an ORP of between 600 mV and 1000 mV with the system, the output water and ozone solution can be utilized to destroy various pathogens, including, but not limited to, algae (e.g., blue-green), bacteria (e.g., *Aeromonas* & Actinomycetes, *Bacillus, Campylobacters, Clostridium botulinum, Escherichia coli (E. coli), Flavobacterium, Helicobacter (pylori)*, Heterotrophic Bacteria, *Legionella pneumophila, Micrococcus, Mycobacterium tuberculosis, Pseudomonas aeruginosa, Salmonella, Shigella shigellosis* (dysentery), *Staphylococcus* sp, *albus, aureus, Streptococcus, Vibrio: alginolyticus, anguillarium, parahemolyticus, Yersinia enterocolitica*), fungi, molds, yeasts, mold spores, nematodes, protozoa (e.g., *Acanthamoeba* & *Naegleria, Amoeboe Trophozoites, Cryptosporidium, Cyclospora, Entamobea (histolytica), Giardia lamblia, Giardia muris, Microsporidium, N. gruberi*), trematodes, viruses (e.g., Adenovirus, Astrovirus, Cailcivirus, Echovirus, Encephalomyocarditis, Enterovirus, coxsachie, poliovirus, Hepatitis A, B and C, Myxovirus influenza, Norwalk, Picobirnavirus, Reovirus, Rotavirus).

The water in the water and ozone solution may have a surface tension of about 72 Millinewtons per meter at 20° C. as it enters the system. The system 100 may be configured to reduce the surface tension of the water in the water and ozone solution to about 48-58 Millinewtons per meter at 20° C. The reduced surface tension of the water enables the water and ozone solution being sprayed onto the hard surfaces and equipment to remove grease more effectively from hard surfaces and equipment since ozonated fluid is more capable of loosening and disintegrating any biofilm on the hard surfaces or equipment. The reduced surface tension of the water in the water and ozone solution better enables the cleansing of the hard surfaces and equipment since it more easily penetrates foreign material on the hard surfaces and equipment.

In some implementations, the system 100 may be used for water treatment or decontamination as described below.

Microbiological organisms/species can reside in water sources, including water intended for drinking recreation. Among the microbiological threats is the protozoan parasite—*Cryptosporidium (Crypto)*. Crypto can be a particular challenge for the water treatment industry, however, ozone can eliminate it. Ozone, molecularly known as $O_3$, is a sanitizer and is relentless in its attack of organic microbes (bacteria, viruses, cysts, etc.). Through a process known as lysing, ozone breaks down cell walls or membranes, where it can then destroy the nucleus of the microbe. In addition to sanitation, ozone can provide for the oxidizing of inorganic material that could be present in water, such as metals (e.g., iron and manganese). Although there are a few stronger oxidizers, ozone is the strongest that is readily available for commercial or residential use. For example, ozone is about 1.5 times stronger than chlorine, and can provide a faster oxidizing action. Furthermore, because of this higher oxidation strength, ozone does not build up a tolerance to microbes unlike other sanitizers, such as chlorine. Within the microbial world protozoa, such as *Crypto*, are some of the most resistant to all types of disinfectants. One reason for this resistance is due to its hard outer protective shell, which must be broken through prior to the microbe being inactivated. *Crypto* can cause a variety of ailments, including abdominal cramping, diarrhea, fever, and nausea that can last as long as a month, according to the Centers for Disease Control and Prevention (CDC). Disinfectants used to ward off *Cryptosporidium* for water treatment applications can include chlorine (liquid state), chloramines, chlorine-dioxide (gaseous state), and ozone. However, their ability to perform this inactivation duty should not be regarded equal, as each sanitizer requires a specific level of concentration and contact time to take effect, as described by the following.

To better determine the specific amount of the disinfectant required to inactivate or destroy a microbe, the Environmental Protection Agency (EPA) has determined Ct Values. These Ct Values are the product of the disinfectant's concentration (C, expressed in mg/L) and the contact time (t, expressed in minutes). These Ct Values are calculated specifically to the percentage of microbial kill or better known as the log reduction, e.g., 1–Log=90.0 percent, 2–Log=99.0 percent or 3–Log=99.9 percent inactivation of the particular microbe. According to the EPA, chlorine dioxide would require a Ct of 226, which would correlate to 226 mg/L, at one minute of contact time, at 25° C. to achieve a 3–Log reduction or 99.9 percent inactivation. Although, ozone would only require a Ct of 7.4, correlating to 7.4 mg/L, to achieve the same 99.9 percent inactivation with the same parameters as chlorine dioxide. Ct is a product of concentration and time, and as such, both can be manipulated, as long as the given Ct Value is obtained for the desired log reduction (e.g., Ozone Ct of 7.4 can be achieved with a concentration 3.7 mg/L for two minutes of time).

*Cryptosporidium* outbreaks in public drinking waters and recreational swimming pools are becoming more and more of an evident issue. Unfortunately, forms of chlorine sanitation are not often the best solution, especially for high organic and inorganic contaminant levels, as they will create chlorine oxidation by-products, such as trihalomethanes (THM) and chloramine derivatives. These by-products are the typical cause of (what most associate as being over chlorinated) the chlorine smell in drinking or pool waters, and are the cause of itchy, smelly skin and burning eyes in pool water. Although with a properly sized system, ozone can be used as the primary sanitizing and oxidizing agent, oxidizing the contaminants completely. Using ozone in this manner would then allow chlorine to be used as the secondary residual sanitizer to satisfy regulatory requirements, without the production of chloramines and chlorine's side effects.

Further, ozone can be used to remove iron and manganese from water, forming a precipitate that can be filtered:

$$2Fe^{2+}+O_3+5H_2O \rightarrow 2Fe(OH)_3(s)+O_2+4H^+$$

$$2Mn^{2+}+2O_3+4H_2O \rightarrow 2MN(OH)_2(s)+2O_2+4H^+$$

Ozone will also reduce dissolved hydrogen sulfide in water to sulfurous acid:

$$3O_3+H_2S \rightarrow 3H_2SO_3+3O_2$$

The reactions involved iron, manganese, and hydrogen sulfide can be especially important in the use of ozone-based well water treatment. Further, ozone will also detoxify cyanides by converting the cyanides to cyanates (on the order of 1,000 times less toxic):

$$CN^-+O_3 \rightarrow CNO^-+O_2$$

Ozone will also completely decompose urea, where recent outbreaks of *E-coli* in lettuce have been impacted by urea:

$$(NH_2)_2CO+O_3 \rightarrow N_2+CO_2+2H_2O$$

Ozonated fluids produced by the ozonated fluid dispensing system 100 were analyzed. During the production of the ozonated fluid, oxygen is drawn in through an ambient air dryer with the drying capacity to supply sufficient oxygen at a minus dew point to the generating system, the generating system accumulates excess volume of high-quality gas, which is stalled or held in the chambers, thereby supplying a consistent maximum volume of gas resulting in an ample supply of gas to the injecting system, thereby assuring zero cavitation at the point of gas-liquid interface. The pressure differential created by the fluid mixing paths reduces the size of the bubbles to a uniformed size bubbles with a spherical geometry that are entrained in the water, thereby lowering the surface tension of the processed fluid. This process makes the fluid act like a surfactant and reduces the surface tension from 72 Millinewtons per meter at 20° C. to a tested surface tension of 48-58 Millinewtons equal to 140° F. or 60° C. hot water. At liquid-gas interfaces, surface tension results from the greater attraction of liquid molecules to each other due to cohesion than to the molecules in the gas due to adhesion. The net effect is an inward force at its surface that causes the liquid to behave as if its surface were covered with a stretched elastic membrane. Thus, the surface becomes under tension from the imbalanced forces, which is probably where the term "surface tension" came from. Because of the relatively high attraction of water molecules for each other through a web of hydrogen bonds, water has a higher surface tension (72.8 Millinewtons per meter at 20° C.) compared to that of most other liquids. Surface tension is an important factor in the phenomenon of capillary action.

In embodiments, the ozonated fluid dispensing system 100 can be employed within any residential or commercial structure to supply water and ozone solution for cleansing, disinfecting, degreasing, and/or water treatment (e.g., water filtering, disinfecting, and/or softening). For example, the system 100 may be configured to receive water from a water source (e.g., a conventional water main/supply line, or the like) through inlet 118, mix the water with ozone, and dispense water and ozone solution through outlet 132. The system 100 may be used for a single application or a plurality of different applications. In residential or commercial applications, the system 100 may be configured to supply ozonated water to one or more taps that receive water from a main water source (e.g., the main water line). In this regard, the system 100 can be employed as a whole home or building water cleansing, disinfecting, degreasing, and/or water treatment solution. Alternatively, the system 100 may be used for a particular zone of a residential or commercial building. In some cases, a plurality of systems 100 can be used to ozonate water in a plurality of zones within a residential or commercial building.

The system 100 can also be used for a variety of applications including, but not limited to: cleansing and/or degreasing hard surfaces such as plastic, glass, ceramic, porcelain, stainless steel, or the like; cleansing and/or degreasing equipment such as food service equipment such as ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, grease traps, or the like; and/or cleansing and/or degreasing HVAC or plumbing systems such as roof top units, air scrubbers, humidifiers, water heaters, water softeners, pumps, or the like. Other examples of equipment that can be coupled to the system 100 may include, but are not limited to, washdown stations (e.g., as described in U.S. Pat. No. 10,232,070), wall washing systems (e.g., as described in U.S. Pat. No. 10,232,071), vegetable and fruit washers (e.g., as described in U.S. Pat. No. 10,238,125), potato washers (e.g., as described in U.S. Pat. No. 10,231,466), carcass/subprimal cleaning systems (e.g., as described in U.S. Pat. No. 10,834,929), wastewater treatment systems, and laundry washing machines (e.g., as described in U.S. Pat. Nos. 10,233,583 and 10,233,584). In an example implementation, the system 100 can be used to supply water and ozone solution to a selected piece of equipment or a combination of equipment via multiple taps.

Figure 5A:
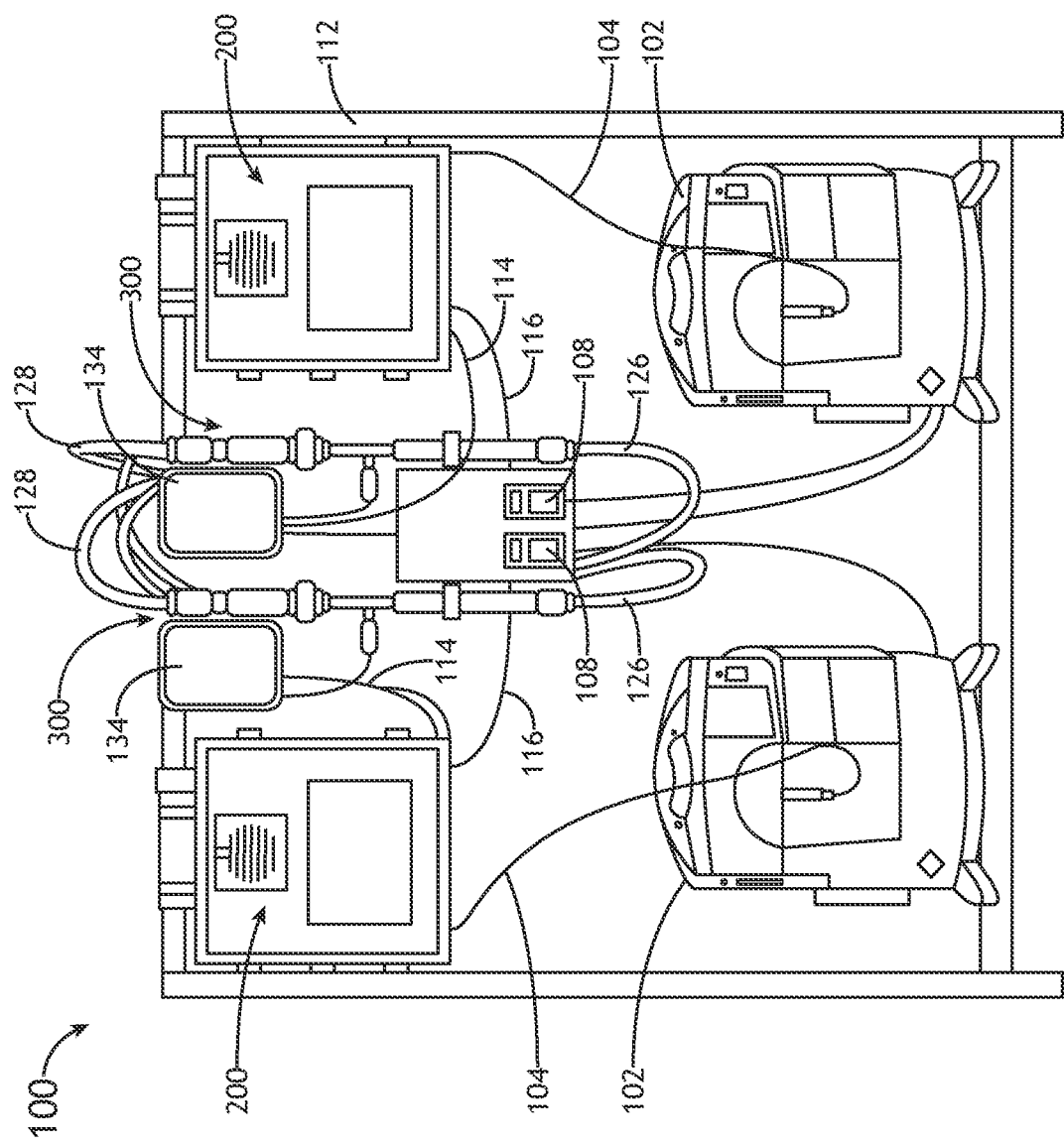
FIG. 5A is a front view of a multi-unit system for creating an oxidation reduction potential (ORP) in water, in accordance with one or more embodiments of this disclosure.
Figure 5B:
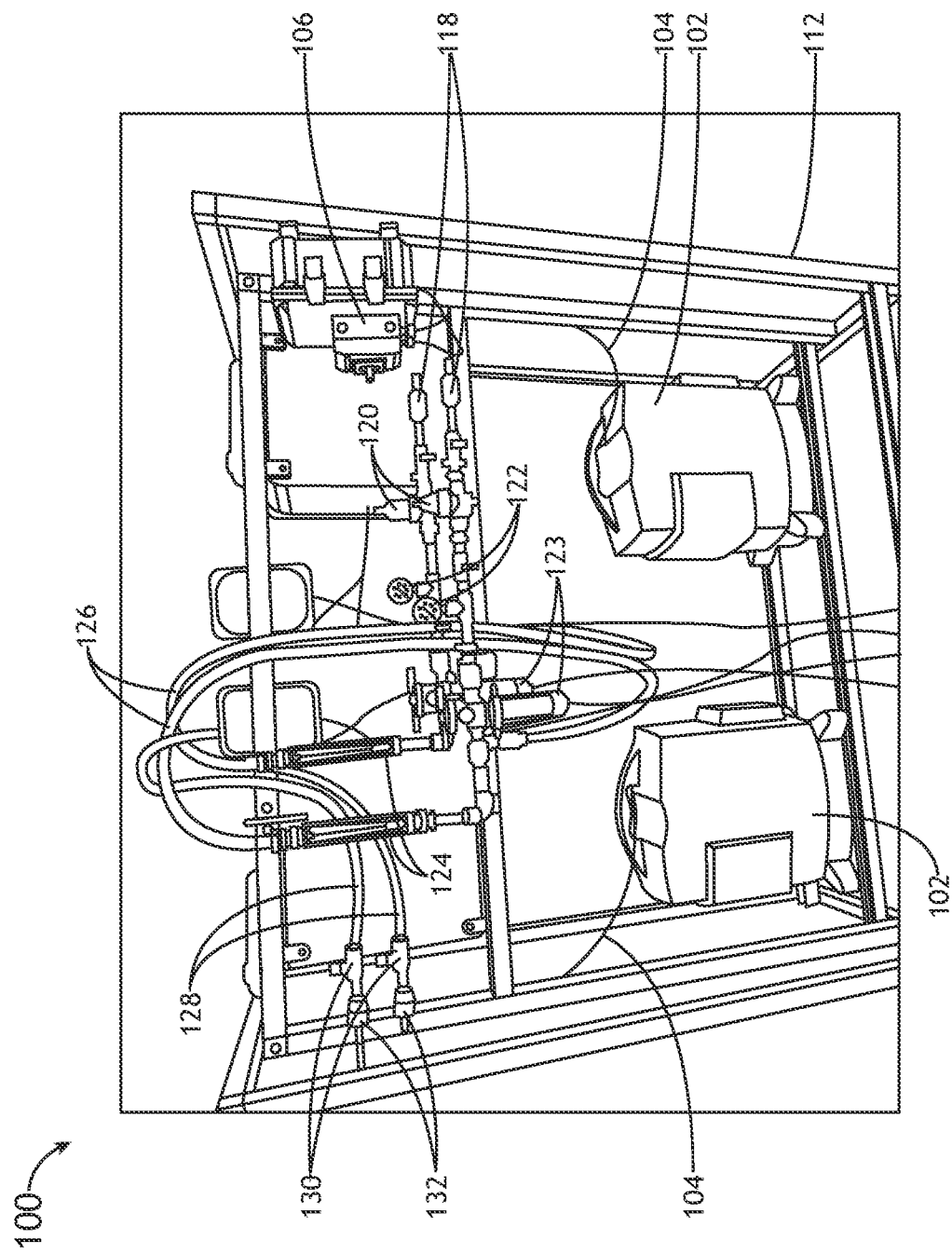
FIG. 5B is a rear view of the multi-unit system for creating an oxidation reduction potential (ORP) in water, in accordance with one or more embodiments of this disclosure.

FIGS. 5A and 5B illustrate a multi-unit embodiment of the system 100. In multi-unit embodiments, the system 100 may include a plurality of ozone supply units 200 and a plurality of pipe assemblies 300 mounted to the transportable support frame 112. Each ozone supply unit 200 may be coupled to respective pipe assembly 300 in the same manner as described above with the embodiments illustrated in FIGS. 1A through 4. In some embodiments, the system 100 may include duplicates of all or most of the components (e.g., components 102 through 134) for each ozone supply unit 200 and pipe assembly 300 set. For example, in FIGS. 5A and 5B, the system 100 includes duplicates of all components except for a shared power switch 106. Alternatively, two or more ozone supply unit 200 and pipe assembly 300 sets may share some auxiliary components. For example, in alternative embodiments (not shown), the system 100 may have a single input path (components 118 through 126) and/or a single output path (components 128 through 132) shared by two or more ozone supply unit 200 and pipe assembly 300 sets. Such configurations may require one or more splitters/combiners coupled to the water input port 310 and/or water output port 312 of the pipe assembly 300.

Although the invention has been described with reference to embodiments illustrated in the attached drawings, equivalents or substitutions may be employed without departing from the scope of the invention as recited in the claims. Components illustrated and described herein are examples of devices and components that may be used to implement embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A transportable system for creating an oxidation reduction potential (ORP) in water, comprising:
    a transportable support frame;
    an ozone supply unit mounted to the transportable support frame, the ozone supply unit comprising:
        a supply unit enclosure having one or more air intake ports and one or more ozone output ports;
        a plurality of ozone generators disposed within the supply unit enclosure, the plurality of ozone generators being fluidically coupled to the one or more air intake ports and the one or more ozone output ports of the supply unit enclosure; and
        one or more controllers disposed within the supply unit enclosure, the one or more controllers being communicatively coupled to the plurality of ozone generators;
    a flow switch configured to transmit one or more control signals to the one or more controllers in response to sensing a flow of water, the one or more controllers being configured to cause the plurality of ozone generators to generate ozone in response to the one or more control signals; and
    a pipe assembly mounted to the transportable support frame, the pipe assembly comprising:
        a first flow path for the water to flow through, the first flow path including one or more ozone intake ports, the one or more ozone intake ports being fluidically coupled to the one or more ozone output ports of the supply unit enclosure, wherein the first flow path is defined by a first set of pipe segments and fittings between a water input port and a water output port of the pipe assembly; and
        a second flow path fluidically coupled in parallel with the first flow path, the second flow path including a control valve that selectively permits a portion of the water to flow through the second flow path to produce a negative pressure in the first flow path so that ozone is drawn into the first flow path through the one or more ozone intake ports and mixed into the water flowing through the first flow path, wherein the second flow path is defined by a second set of pipe segments and fittings that form a D shaped branch out of the first flow path.

2. The transportable system of claim 1, further comprising:
    an oxygen concentrator configured to supply oxygen-enriched air to the one or more air intake ports of the ozone supply unit.

3. The transportable system of claim 2, wherein the ozone supply unit further comprises an air dryer externally coupled to the supply unit enclosure, the air dryer being configured to remove moisture from the oxygen-enriched air before the oxygen-enriched air is supplied to the plurality of ozone generators through the one or more air intake ports.

4. The transportable system of claim 1, wherein the supply unit enclosure and the pipe assembly are fluidically coupled by one or more tubes for transferring ozone from the supply unit enclosure to the pipe assembly.

5. The transportable system of claim 4, further comprising:
    a solenoid valve configured to purge residual ozone from the one or more tubes.

6. The transportable system of claim 1, wherein the flow switch is fluidically coupled to a third flow path in parallel with the first and second flow paths of the pipe assembly.

7. The transportable system of claim 1, wherein the first flow path includes a fluid mixer.

8. The transportable system of claim 7, wherein the fluid mixer is removably coupled between two pipe fittings.

9. The transportable system of claim 7, wherein the fluid mixer comprises a multi-port coupler including a water inlet, a water outlet, and an ozone input port.

10. The transportable system of claim 9, wherein the multi-port coupler comprises a venturi.

11. The transportable system of claim 1, further comprising:
    one or more ORP monitors configured to detect an ORP of water and ozone solution output by the pipe assembly.

12. The transportable system of claim 1, wherein the supply unit enclosure and the pipe assembly are independently locatable, separate structures.

13. The transportable system of claim 1, further comprising:
    a support bracket for mounting the pipe assembly to the transportable support frame.

14. The transportable system of claim 1, wherein the transportable support frame is a wheeled support frame.

15. The transportable system of claim 1, wherein the control valve is adjustable to vary the negative pressure produced in the first flow path in order to control an ozone concentration of the aqueous ozone solution.

16. A transportable multi-unit system for creating an oxidation reduction potential (ORP) in water, comprising:
   a transportable support frame;
   a plurality of ozone supply units mounted to the transportable support frame, each ozone supply unit comprising:
      a supply unit enclosure having one or more air intake ports and one or more ozone output ports;
      a plurality of ozone generators disposed within the supply unit enclosure, the plurality of ozone generators being fluidically coupled to the one or more air intake ports and the one or more ozone output ports of the supply unit enclosure; and
      one or more controllers disposed within the supply unit enclosure, the one or more controllers being communicatively coupled to the plurality of ozone generators;
   one or more flow switches configured to transmit one or more control signals to the one or more controllers in response to sensing a flow of water, the one or more controllers being configured to cause the plurality of ozone generators to generate ozone in response to the one or more control signals; and
   a plurality of pipe assemblies mounted to the transportable support frame, each pipe assembly comprising:
      a first flow path for the water to flow through, the first flow path including one or more ozone intake ports, the one or more ozone intake ports being fluidically coupled to the one or more ozone output ports of the supply unit enclosure, wherein the first flow path is defined by a first set of pipe segments and fittings between a water input port and a water output port of the pipe assembly; and
      a second flow path fluidically coupled in parallel with the first flow path, the second flow path including a control valve that selectively permits a portion of the water to flow through the second flow path to produce a negative pressure in the first flow path so that ozone is drawn into the first flow path through the one or more ozone intake ports and mixed into the water flowing through the first flow path, wherein the second flow path is defined by a second set of pipe segments and fittings that form a D shaped branch out of the first flow path.

17. The transportable multi-unit system of claim 16, wherein the plurality of supply unit enclosures and the plurality of pipe assemblies are independently locatable, separate structures.

18. The transportable multi-unit system of claim 16, further comprising:
   a plurality of support brackets for mounting the plurality of pipe assemblies to the transportable support frame.

19. The transportable multi-unit system of claim 16, wherein the transportable support frame is a wheeled support frame.

20. The transportable multi-unit system of claim 16, wherein the control valve is adjustable to vary the negative pressure produced in the first flow path in order to control an ozone concentration of the aqueous ozone solution.

* * * * *